United States Patent
Branch et al.

(10) Patent No.: US 7,405,217 B2
(45) Date of Patent: *Jul. 29, 2008

(54) N-AROYL PIPERAZINE DERIVATIVES AS OREXIN RECEPTOR ANTAGONISTS

(75) Inventors: Clive Leslie Branch, Harlow (GB); Christopher Norbert Johnson, Harlow (GB); David John Nash, Harlow (GB); Geoffrey Stemp, Harlow (GB)

(73) Assignee: SmithKline Beecham p.l.c., Brentford, Middlesex (GB)

( * ) Notice: Subject to any disclaimer, the term of this patent is extended or adjusted under 35 U.S.C. 154(b) by 0 days.

This patent is subject to a terminal disclaimer.

(21) Appl. No.: 11/557,998

(22) Filed: Nov. 9, 2006

(65) Prior Publication Data

US 2007/0167457 A1  Jul. 19, 2007

Related U.S. Application Data

(63) Continuation of application No. 10/492,250, filed as application No. PCT/EP02/11316 on Oct. 9, 2002, now Pat. No. 7,166,608.

(30) Foreign Application Priority Data

Oct. 11, 2001 (GB) ................................ 0124463.1

(51) Int. Cl.
*A61K 31/495* (2006.01)
*A61K 31/496* (2006.01)
*C07D 241/04* (2006.01)
*C07D 417/12* (2006.01)

(52) U.S. Cl. ............................ 514/254.02; 514/254.03; 544/180; 544/182; 544/238; 544/295; 544/350; 544/353; 544/355; 544/357; 544/360; 544/362; 544/363; 544/364; 544/367; 544/368; 544/391

(58) Field of Classification Search .................. 544/367, 544/369; 514/254.02, 254.03
See application file for complete search history.

(56) References Cited

U.S. PATENT DOCUMENTS

| | | | |
|---|---|---|---|
| 6,677,354 B2 * | 1/2004 | Branch et al. ................ 514/318 |
| 6,943,160 B2 * | 9/2005 | Branch et al. ............ 514/235.2 |
| 7,166,608 B2 * | 1/2007 | Branch et al. .......... 514/254.02 |

FOREIGN PATENT DOCUMENTS

| | | |
|---|---|---|
| JP | 8-40999 | 2/1996 |
| WO | WO 98/57954 | 12/1998 |
| WO | WO 01/25219 | 4/2001 |
| WO | WO 01/96302 | 12/2001 |
| WO | WO 02/44172 | 6/2002 |
| WO | WO 02/089800 | 11/2002 |
| WO | WO 02/090355 | 11/2002 |
| WO | 03/032991 * | 4/2003 |

OTHER PUBLICATIONS

Langmead et al. *Br. J. Pharmacol..*, 141: 340-346 (2004).
Porter et al. *Bioorg. & Med. Chem. Lett.*, 11: 1907-1910 (2001).
Duxon et al. *Psychopharmacology*, 153: 203-209 (2001).
White et al. *Peptides*, 26: 2331-2338 (2005).
Ishii et al. *Behav. Brain Res.*, 160: 11-24 (2005).
Ishii et al. *Behav. Brain Res.*, 157: 331-341 (2005).
Ishii et al. *Physiol. & Behav.*; 81: 129-140 (2004).
Smith et al. *Neurosci.*, 341: 256-258 (2003).
Haynes et al. *Regulatory Peptides*, 104: 153-159 (2002).
Bingham et al. *Pain*, 92: 81-90 (2001).
Rodgers et al. *Eur. J. Neurosci.*, 13: 1444-1452 (2001).
Smart et al. *Br. J. Pharmacol.*, 132: 1179-1182 (2001).
Jones et al. *Psychopharmacology*, 153: 210-218 (2001).
Haynes et al. *Regulatory Peptides*, 96: 45-51 (2000).
Rodgers et al. *Neuropeptides*, 36(5): 303-325 (2002).
Cai et al. *Expert Opin. Ther. Patents*, 16: 631-646 (2006).
Fujii et al. *Chemical Abstracts*, 124(No. 34333): Abstract for JP 08040999 (1996).
USPTO office action dated Oct. 10, 2007, U.S. Appl. No. 10/481,133.

* cited by examiner

*Primary Examiner*—Emily Bernhardt
(74) *Attorney, Agent, or Firm*—Kathryn L. Sieburth; Mary E. McCarthy; Charles M. Kinzig

(57) ABSTRACT

This invention relates to N-aroyl cyclic amino derivatives and their use as pharmaceuticals.

14 Claims, No Drawings

N-AROYL PIPERAZINE DERIVATIVES AS OREXIN RECEPTOR ANTAGONISTS

This application is a continuation of application Ser. No. 10/492,250, filed Jul. 2, 2004, now U.S. Pat. No. 7,166,608, which is a 371 of International Application No. PCT/EP02/11316, filed Oct. 9, 2002.

This invention relates to N-aroyl cyclic amine derivatives and their use as pharmaceuticals.

Many medically significant biological processes are mediated by proteins participating in signal transduction pathways that involve G-proteins and/or second messengers.

Polypeptides and polynucleotides encoding the human 7-transmembrane G-protein coupled neuropeptide receptor, orexin-1 (HFGAN72), have been identified and are disclosed in EP-A-875565, EP-A-875566 and WO 96/34877. Polypeptides and polynucleotides encoding a second human orexin receptor, orexin-2 (HFGANP), have been identified and are disclosed in EP-A-893498.

Polypeptides and polynucleotides encoding polypeptides which are ligands for the orexin-1 receptor, e.g. orexin-A (Lig72A) are disclosed in EP-A-849361.

Orexin receptors are found in the mammalian host and may be responsible for many biological functions, including pathologies including, but not limited to, depression; anxiety; addictions; obsessive compulsive disorder; affective neurosis/disorder; depressive neurosis/disorder; anxiety neurosis; dysthymic disorder; behaviour disorder; mood disorder; sexual dysfunction; psychosexual dysfunction; sex disorder; sexual disorder; schizophrenia; manic depression; delerium; dementia; severe mental retardation and dyskinesias such as Huntington's disease and Gilles de la Tourett's syndrome; disturbed biological and circadian rhythms; feeding disorders, such as anorexia, bulimia, cachexia, and obesity; diabetes; appetite/taste disorders; vomiting/nausea; asthma; cancer; Parkinson's disease; Cushing's syndrome/disease; basophil adenoma; prolactinoma; hyperprolactinemia; hypopituitarism; hypophysis tumor/adenoma; hypothalamic diseases; Froehlich's syndrome; adrenohypophysis disease; hypophysis disease; hypophysis tumor/adenoma; pituitary growth hormone; adrenohypophysis hypofunction; adrenohypophysis hyperfunction; hypothalamic hypogonadism; Kallman's syndrome (anosmia, hyposmia); functional or psychogenic amenorrhea; hypopituitarism; hypothalamic hypothyroidism; hypothalamic-adrenal dysfunction; idiopathic hyperprolactinemia; hypothalamic disorders of growth hormone deficiency; idiopathic growth hormone deficiency; dwarfism; gigantism; acromegaly; disturbed biological and circadian rhythms; and sleep disturbances associated with such diseases as neurological disorders, neuropathic pain and restless leg syndrome, heart and lung diseases; acute and congestive heart failure; hypotension; hypertension; urinary retention; osteoporosis; angina pectoris; myocardial infarction; ischaemic or haemorrhagic stroke; subarachnoid haemorrhage; head injury such as sub-arachnoid haemorrhage associated with traumatic head injury; ulcers; allergies; benign prostatic hypertrophy; chronic renal failure; renal disease; impaired glucose tolerance; migraine; hyperalgesia; pain; enhanced or exaggerated sensitivity to pain, such as hyperalgesia, causalgia and allodynia; acute pain; burn pain; atypical facial pain; neuropathic pain; back pain; complex regional pain syndromes I and II; arthritic pain; sports injury pain; pain related to infection, e.g. HIV, post-polio syndrome, and post-herpetic neuralgia; phantom limb pain; labour pain; cancer pain; post-chemotherapy pain; post-stroke pain; post-operative pain; neuralgia; conditions associated with visceral pain including irritable bowel syndrome, migraine and angina; urinary bladder incontinence e.g. urge incontinence; tolerance to narcotics or withdrawal from narcotics; sleep disorders; sleep apnea; narcolepsy; insomnia; parasomnia; jet-lag syndrome; and neurodegenerative disorders, which includes nosological entities such as disinhibition-dementia-parkinsonism-amyotrophy complex; pallido-ponto-nigral degeneration, epilepsy, and seizure disorders.

Experiments have shown that central administration of the ligand orexin-A (described in more detail below) stimulated food intake in freely-feeding rats during a 4 hour time period. This increase was approximately four-fold over control rats receiving vehicle. These data suggest that orexin-A may be an endogenous regulator of appetite. Therefore, antagonists of its receptor may be useful in the treatment of obesity and diabetes, see Cell, 1998, 92, 573-585.

There is a significant incidence of obesity in westernised societies. According to WHO definitions a mean of 35% of subjects in 39 studies were overweight and a further 22% clinically obese. It has been estimated that 5.7% of all healthcare costs in the USA are a consequence of obesity. About 85% of Type 2 diabetics are obese, and diet and exercise are of value in all diabetics. The incidence of diagnosed diabetes in westernised countries is typically 5% and there are estimated to be an equal number undiagnosed. The incidence of both diseases is rising, demonstrating the inadequacy of current treatments which may be either ineffective or have toxicity risks including cardiovascular effects. Treatment of diabetes with sulfonylureas or insulin can cause hypoglycaemia, whilst metformin causes GI side-effects. No drug treatment for Type 2 diabetes has been shown to reduce the long-term complications of the disease. Insulin sensitisers will be useful for many diabetics, however they do not have an anti-obesity effect.

Rat sleep/EEG studies have also shown that central administration of orexin-A, an agonist of the orexin receptors, causes a dose-related increase in arousal, largely at the expense of a reduction in paradoxical sleep and slow wave sleep 2, when administered at the onset of the normal sleep period. Therefore antagonists of its receptor may be useful in the treatment of sleep disorders including insomnia.

The present invention provides N-aroyl cyclic amine derivatives which are non-peptide antagonists of human orexin receptors, in particular orexin-1 receptors. In particular, these compounds are of potential use in the treatment of obesity, including obesity observed in Type 2 (non-insulin-dependent) diabetes patients, and/or sleep disorders. Additionally these compounds are useful in stroke, particularly ischemic or haemorrhagic stroke, and/or blocking the emetic response i.e. the compounds are useful in the treatment of nausea and vomiting.

International Patent Applications WO99/09024, WO99/58533, WO00/47577 and WO00/47580 disclose phenyl urea derivatives and WO00/47576 discloses quinolinyl cinnamide derivatives as orexin receptor antagonists. WO01/96302 discloses N-aroyl cyclic amine derivatives and WO02/44172 discloses morpholine derivatives as orexin receptor antagonists.

According to the invention there is provided a compound of formula (I):

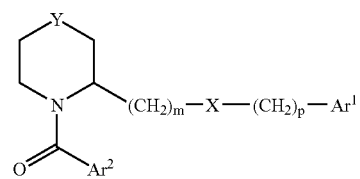

(I)

wherein:

Y represents $NR^2$;

m represents 1, 2, or 3;

p represents 0 or 1;

X is O, S, C=O, $SO_2$, or —CH=CH—;

$Ar^1$ is aryl, or a mono or bicyclic heteroaryl group containing up to 4 heteroatoms selected from N, O and S; any of which may be optionally substituted;

$Ar^2$ represents phenyl or a 5- or 6-membered heterocyclyl group containing 1 to 3 heteroatoms selected from N, O and S, wherein the phenyl or heterocyclyl group is substituted by $R^1$ and further optional substituents; or $Ar^2$ represents an optionally substituted bicyclic aromatic or bicyclic heteroaromatic group containing 1 to 4 heteroatoms selected from N, O and S;

$R^1$ represents optionally substituted $(C_{1-4})$alkoxy, halo, optionally substituted $(C_{1-6})$alkyl, optionally substituted phenyl, or an optionally substituted 5- or 6-membered heterocyclic ring containing 1 to 4 heteroatoms selected from N, O and S;

$R^2$ represents hydrogen, optionally substituted $(C_{1-4})$alkyl, optionally substituted $(C_{1-6})$alkanoyl, optionally substituted $(C_{1-6})$alkanoxycarbonyl or optionally substituted aryl$(C_{1-6})$alkyloxycarbonyl;

or a pharmaceutically acceptable salt thereof.

Preferably where $Ar^2$ represents phenyl or a 5- or 6-membered heterocyclyl group containing up to 3 heteroatoms selected from N, O and S, the $R^1$ group is situated adjacent to the point of attachment to the amide carbonyl.

Preferably $Ar^1$ is aryl, or a mono or bicyclic heteroaryl group containing up to 3 heteroatoms selected from N, O and S; any of which may be optionally substituted.

$R^2$ can represent hydrogen, or optionally substituted $(C_{1-4})$alkyl.

Preferably $R^2$ is hydrogen, methyl, ethyl, acetyl, trifluoroacetyl, methoxycarbonyl or benzyloxycarbonyl. More preferably $R^2$ is hydrogen, methyl or ethyl, even more preferably hydrogen or methyl.

Preferably $Ar^2$ represents phenyl or a 5- or 6-membered heterocyclyl group containing up to 3 heteroatoms selected from N, O and S, wherein the phenyl or heterocyclyl group is substituted by $R^1$ and further optional substituents; or $Ar^2$ represents an optionally substituted bicyclic aromatic or bicyclic heteroaromatic group containing up to 3 heteroatoms selected from N, O and S.

Preferably when $R^1$ represents an optionally substituted 5- or 6-membered heterocyclic ring it contains up to 3 heteroatoms selected from N, O and S.

Preferably $R^1$ is selected from trifluoromethoxy, methoxy, halo, or an optionally substituted phenyl, pyridinyl, pyrazolyl, oxadiazolyl, or pyrimidinyl group.

More preferably $R^1$ represents an optionally substituted phenyl, pyridinyl, pyrazolyl or oxadiazolyl or pyrimidinyl group.

Even more preferably $R^1$ represents an optionally substituted phenyl.

When $Ar^1$ is optionally substituted aryl it is preferably phenyl or naphthyl. The aryl group may have up to 5, preferably 1, 2 or 3 optional substituents.

When $Ar^1$ is a mono or bicyclic heteroaryl group it is for example quinoxalinyl, quinazolinyl, pyridopyrazinyl, benzoxazolyl, benzothiophenyl, benzimidazolyl, naphthyridinyl, pyridinyl, pyrimidinyl, thiazolyl, or benzofuranyl.

Preferably $Ar^1$ is an optionally substituted phenyl.

Preferably m is 2 and p is 0.

Preferably X is O.

When $Ar^2$ or $R^1$ is a 5- or 6-membered heterocyclyl group containing up to 3 heteroatoms selected from N, O and S, it may be furanyl, thienyl, pyrrolyl, oxazolyl, thiazolyl, imidazolyl, oxadiazolyl, thiadiazolyl, pyridinyl, triazolyl, triazinyl, pyridazinyl, pyrimidinyl, isothiazolyl, isoxazolyl, pyrazinyl, or pyrazolyl.

When $Ar^2$ represents an optionally substituted bicyclic aromatic or bicyclic heteroaromatic group example are benzofuranyl, benzimidazolyl, quinolinyl, quinoxalinyl, or naphthyl.

Preferably $Ar^2$ represents optionally substituted phenyl, pyridinyl, thiazolyl, pyrazolyl, pyridazinyl, 1,2,3-triazolyl or napthyl. Alternatively $Ar^2$ represents optionally substituted phenyl, pyridinyl, thiazolyl, pyrazolyl, pyridazinyl or 1,2,3-triazolyl.

Most preferably $Ar^2$ is thiazolyl.

Optional substituents for the groups $Ar^1$, $Ar^2$ and $R^1$ include halogen, hydroxy, oxo, cyano, nitro, $(C_{1-4})$alkyl, $(C_{1-4})$ alkoxy, halo$(C_{1-4})$alkyl, halo$(C_{1-4})$alkoxy, aryl$(C_{1-4})$alkoxy, $(C_{1-4})$alkylthio, hydroxy$(C_{1-4})$alkyl, $(C_{1-4})$alkoxy$(C_{1-4})$alkyl, $(c_{3-6})$cycloalkyl$(C_{1-4})$alkoxy, $(C_{1-4})$alkanoyl, $(C_{1-4})$alkoxycarbonyl, $(C_{1-4})$alkylsulfonyl, $(C_{1-4})$alkylsulfonyloxy, $(C_{1-4})$alkylsulfonyl$(C_{1-4})$alkyl, arylsulfonyl, arylsulfonyloxy, arylsulfonyl$(C_{1-4})$alkyl, $(C_{1-4})$alkylsulfonamido, $(C_{1-4})$alkylamido, $(C_{1-4})$alkylsulfonamido$(C_{1-4})$alkyl, $(C_{1-4})$alkylamido$(C_{1-4})$alkyl, arylsulfonamido, arylcarboxamido, arylsulfonamido$(C_{1-4})$alkyl, arylcarboxamido$(C_{1-4})$alkyl, aroyl, aroyl$(C_{1-4})$alkyl, or aryl$(C_{1-4})$alkanoyl group; a group $R^3R^4N$—, $R^3OCO(CH_2)_r$, $R^3CON(R^4)(CH_2)_r$, $R^3R^4NCO(CH_2)_r$, $R^3R^4NSO_2(CH_2)_r$, or $R^3SO_2NR^4(CH_2)_r$ where each of $R^3$ and $R^4$ independently represents a hydrogen atom or a $(C_{1-4})$alkyl group or where appropriate $R^3R^4$ forms part of a $(C_{3-6})$azacyloalkane or $(C_{3-6})$(2-oxo)azacycloalkane ring and r represents zero or an integer from 1 to 4. Additional substituents are $(C_{1-4})$acyl, aryl, aryl$(C_{1-4})$alkyl, $(C_{1-4})$alkylamino$(C_{1-4})$alkyl, $R^3R^4N(CH_2)n$-, $R^3R^4N(CH_2)nO$—, wherein n represents an interger from 1 to 4. Additionally when the substituent is $R^3R^4N(CH_2)n$- or $R^3R^4N(CH_2)nO$, $R^3$ with at least one $CH_2$ of the $(CH_2)n$ portion of the group form a $(C_{3-6})$azacycloalkane and $R^4$ represents hydrogen, a $(C_{1-4})$alkyl group or with the nitrogen to which it is attached forms a second $(C_{3-6})$azacycloalkane fused to the first $(C_{3-6})$azacycloalkane.

In addition $Ar^1$ may be optionally substituted by a phenyl ring optionally substituted by a halogen, cyano, $C_{1-4}$alkanoyl or $C_{1-4}$alkylsulfonyl group; or by a 5- or 6-membered heterocyclic ring, optionally substituted by a $(C_{1-2})$alkyl or $R^3R^4N$— group; wherein $R^3$ and $R^4$ are as defined above.

Preferred optional substituents for $Ar^2$ include halogen, cyano, $(C_{1-4})$alkanoyl and optionally substituted $(C_{1-6})$alkyl.

Preferably $Ar^2$ is optionally substituted by halogen, cyano, or optionally substituted $(C_{1-6})$alkyl.

Preferred optional substituents for $Ar^1$ include halogen.

Preferred compounds are selected from:

(RS)-2-(2-(4-Fluoro)phenoxyethyl)-1-((4-(2-methyl-5-phenyl)thiazolyl)carbonyl)-4-trifluoroacetylpiperazine;

(RS)-4-Methyl-1-((4-(2-methyl-5-phenyl)thiazolyl)carbonyl)-2-(2-phenoxyethyl) piperazine;

(RS)-2-(2-(4-Fluoro)phenoxyethyl)-1-((4-(2-methyl-5-phenyl)thiazolyl) carbonyl)piperazine;

(RS)-4-Methyl-2-(2-phenoxyethyl)-1-((2-phenyl)benzamido)-piperazine;

(RS)-4-(Benzyloxycarbonyl)-1-((2-(3-methyl-[1,2,4]-oxadiazol-5-yl)-phenyl)carbonyl)-2-(2)-phenoxyethyl)piperazine;

(RS)-4-(Benzyloxycarbonyl)-1-((4-(2-methyl-5-phenyl)thiazolyl)carbonyl)-2-(2-phenoxyethyl)piperazine;

(RS)-4-(Methoxycarbonyl)-1-((2-phenyl)benzamido)-2-(2-phenoxyethyl)piperazine;
(RS)-4-(Methoxycarbonyl)-1-((4-(2-methyl-5-phenyl)thiazolyl)carbonyl)-2-(2-phenoxyethyl)piperazine;
(RS)-4-(Methoxycarbonyl)-1-((1-naphthyl)carbonyl)-2-(2-phenoxyethyl)piperazine;
(RS)-4-Acetyl-1-((4-(2-methyl-5-phenyl)thiazolyl)carbonyl)-2-(2-phenoxyethyl)piperazine; or
(RS)-1-((2-Phenyl)benzamido)-2-(2-phenoxyethyl)piperazine acetate and pharmaceutically acceptable salts thereof.

In the groups $Ar^1$ and $Ar^2$, substituents positioned ortho to one another may be linked to form a ring.

When a halogen atom is present in the compound of formula (I) it may be fluorine, chlorine, bromine or iodine. When the compound of formula (I) contains an alkyl group, whether alone or forming part of a larger group, e.g. alkoxy or alkylthio, the alkyl group may be straight chain, branched or cyclic, or combinations thereof, it is preferably methyl or ethyl.

When used herein the term aryl includes phenyl, or a 8- to 12-membered bicyclic ring system where at least one of the rings is aromatic for example naphthyl.

When X represents a group —CH═CH—, the compounds of formula (I) may exist as geometric isomers around the double bond. The present invention includes within its scope all such isomers, including mixtures.

It will be appreciated that compounds of formula (I) may exist as R or S enantiomers. The present invention includes within its scope all such isomers, including mixtures. Where additional chiral centres are present in compounds of formula (I), the present invention includes within its scope all possible diastereoismers, including mixtures thereof. The different isomeric forms may be separated or resolved one from the other by conventional methods, or any given isomer may be obtained by conventional synthetic methods or by stereospecific or asymmetric syntheses.

It will be understood that the invention includes pharmaceutically acceptable derivatives of compounds of formula (I) and that these are included within the scope of the invention.

Particular compounds according to the invention include those mentioned in the examples and their pharmaceutically acceptable derivatives.

As used herein "pharmaceutically acceptable derivative" includes any pharmaceutically acceptable salt, ester or salt of such ester of a compound of formula (I) which, upon administration to the recipient is capable of providing (directly or indirectly) a compound of formula (I) or an active metabolic or residue thereof.

It will be appreciated that for use in medicine the salts of the compounds of formula (I) should be pharmaceutically acceptable. Suitable pharmaceutically acceptable salts will be apparent to those skilled in the art and include acid addition salts formed with inorganic acids e.g. hydrochloric, hydrobromic, sulphuric, nitric or phosphoric acid; and organic acids e.g. succinic, maleic, acetic, fumaric, citric, tartaric, benzoic, p-toluenesulfonic, methanesulfonic or naphthalenesulfonic acid. Other salts e.g. oxalates, may be used, for example in the isolation of compounds of formula (I) and are included within the scope of this invention. Also included within the scope of the invention are solvates and hydrates of compounds of formula (I).

Certain of the compounds of formula (I) may form acid addition salts with one or more equivalents of the acid. The present invention includes within its scope all possible stoichiometric and non-stoichiometric forms.

Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

According to a further feature of the invention there is provided a process for the preparation of compounds of formula (I) and salts thereof. The following schemes detail some synthetic routes to compounds of the invention.

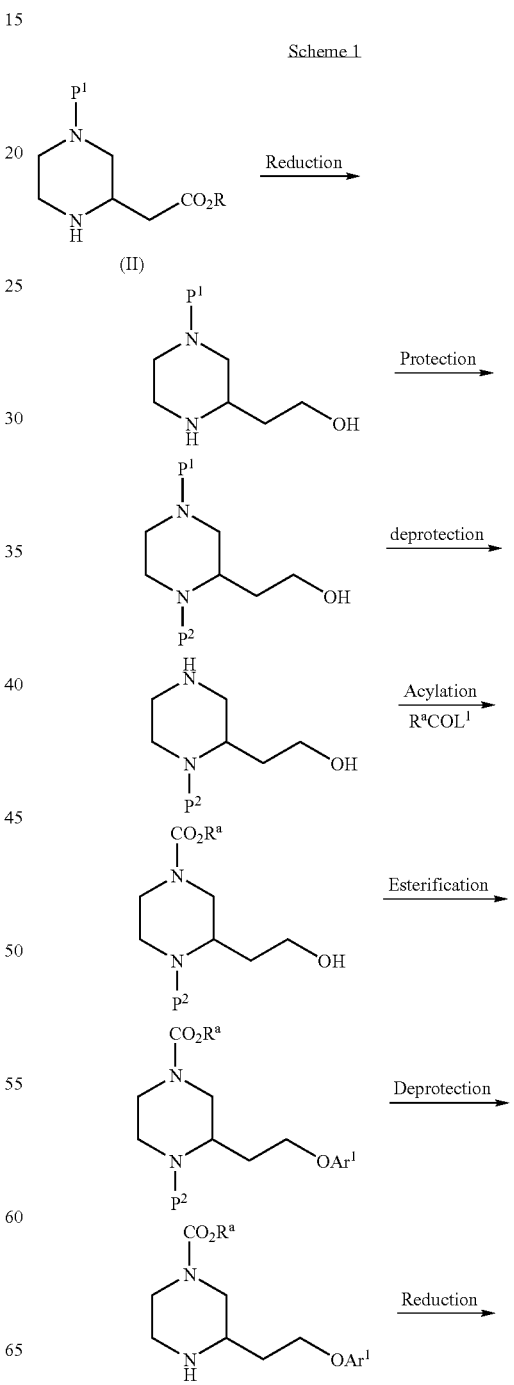

Scheme 1

-continued

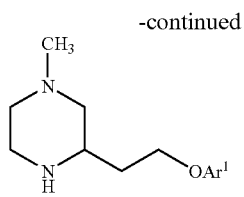

Scheme 2

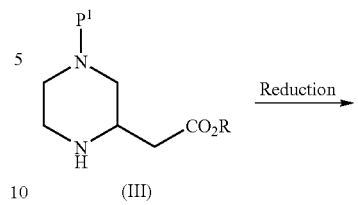

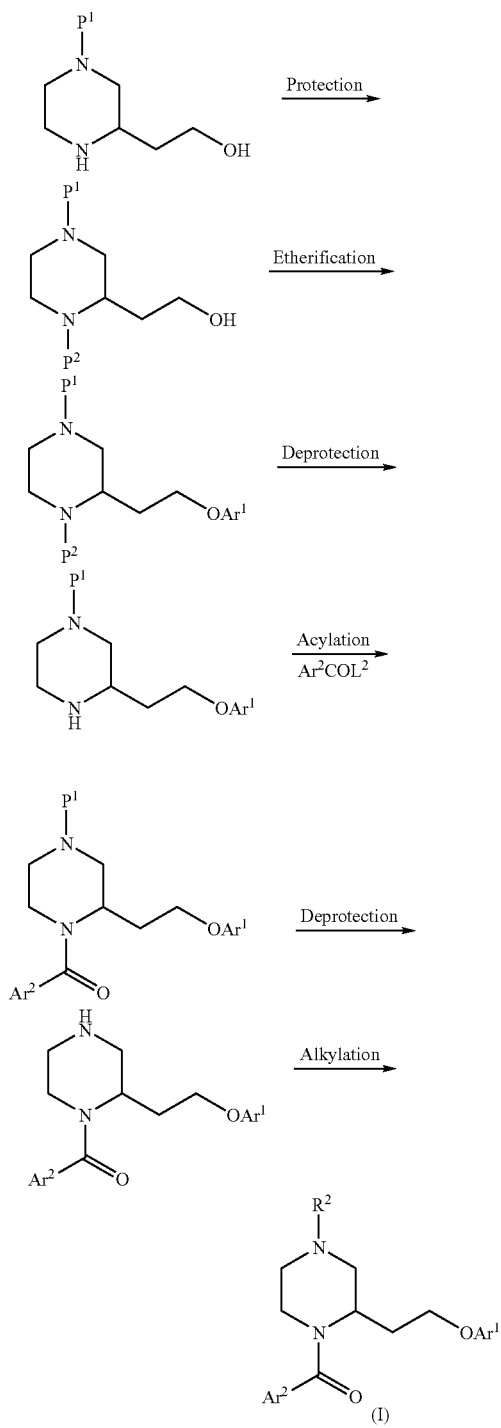

wherein Ar¹ and Ar² are as defined for compounds of formula (I), R and $R^a$ are optionally substituted alkyl groups, P¹ and P² are protecting groups and L¹ and L² are leaving groups.

Examples of protecting groups P¹ and P² include t-butyloxycarbonyl, trifluoroacetyl, benzyloxycarbonyl and optionally substituted benzyl. Deprotection conditions will depend on the particular protecting group; for the groups mentioned above these are respectively, acid (e.g. trifluoroacetic acid in dichloromethane), base (e.g. potassium carbonate in a solvent such as aqueous methanol) and catalytic hydrogenolysis in an inert solvent (e.g. using palladium on charcoal in a lower alcohol or ethyl acetate).

Examples of suitable leaving groups L¹ include halogen and for L² include halogen, hydroxy, OC(=O)alkyl OC(=O)O-alkyl and OSO₂Me. Acylation may be carried out using a wide range of known conditions, e.g. in an inert solvent such as dichloromethane, in the presence of a base such as triethylamine. Alternatively these steps may be carried out when L² represents hydroxy, in which case the reaction takes place in an inert solvent such as dichloromethane in the presence of a diimide reagent such as 1-ethyl-3-(3-dimethylaminopropyl)carbodiimide hydrochloride, and an activator such as 1-hydroxy-benzo-triazole.

Reduction of the ester can be carried out using known methods e.g. with a metal hydride reducing agent such as lithium aluminium hydride in an inert solvent such as diethyl ether or tetrahydrofuran.

Etherification may be carried out using known methods e.g. under Mitsonobu conditions, i.e. in an inert solvent such as dichloromethane or tetrahydrofuran, in the presence of a phosphine reagent such as triphenylphosphine or tributylphosphine, and an azodicarbonyl reagent such as diethyl azodicarboxylate, diisopropyl azodicarboxylate, or 1,1'-azodicarbonyldipiperidine.

Included within the scope is protecting group interchange and use of optional protecting groups within Ar¹, Ar², R¹, R², and Y for example when Y is NH, preferably a protecting group is used.

wherein $Ar^1$, $Ar^2$ are as defined for formula (I), $R^2$ is an optionally substituted $(C_{1-4})$alkyl, R is an optionally substituted alkyl group, $P^1$ and $P^2$ are protecting groups and $L^2$ is a leaving group as defined for scheme 1. For compounds where $R^2$ is hydrogen the final alkylation step is not carried out.

N-Alkylation can be carried out using known conditions: e.g. reductive amination for example using formaldehyde and a metal hydride reducing agent such as sodium triacetoxyborohydride in an inert solvent such as 1,2-dichloromethane.

Within schemes 1 and 2 the protecting groups $P^1$ and $P^2$ are chosen to be different and there is scope for functional group interchange.

Included within the scope is protecting group interchange and use of optional protecting groups within $Ar^1$, $Ar^2$, $R^1$, $R^2$, and Y for example when Y is NH, preferably a protecting group is used.

Compounds of formula (II) and (III) are known in the literature or can be prepared by known methods.

Conversion of one compound of formula (I) to another of formula (I) by interconversion of substituents (including interconversions of the residue X) can be effected.

When $R^1$ is an aromatic group, the substituent $R^1$ may be introduced at the final stage as illustrated in Scheme 3 by reaction of a compound of formula VII) where $L^3$ represents a leaving group such as halogen (preferably bromo or iodo) or trifluoromethylsulfonyloxy, and all other variables are as previously defined, with a reagent $R^1M$, where M is the residue of an organometallic species e.g. $B(OH)_2$ or trialkylstannyl. Such a process may be carried out in an inert solvent such as 1,2-dimethoxyethane or 1,4-dioxan, in the presence of a transition metal catalyst such as $Pd(PPh_3)_4$.

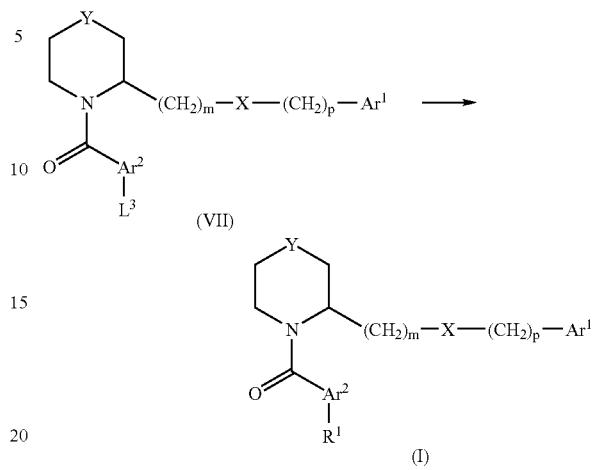

Scheme 3 wherein $Ar^2$, $Ar^1$ X, m and p are as defined for formula (I) and $R^1$ is an aromatic group, Y is N-P wherein P is a protecting group, $L^3$ is a leaving group such as halogen (preferably bromo or iodo) or trifluoromethylsulfonyloxy.

Included within the scope is protecting group interchange and use of optional protecting groups within $Ar^1$, $Ar^2$, $R^1$, $R^2$, and Y for example when Y is NH, preferably a protecting group is used.

Compounds of formula (I) where X represents —CH=CH— may be synthesised by the route shown in Scheme 4.

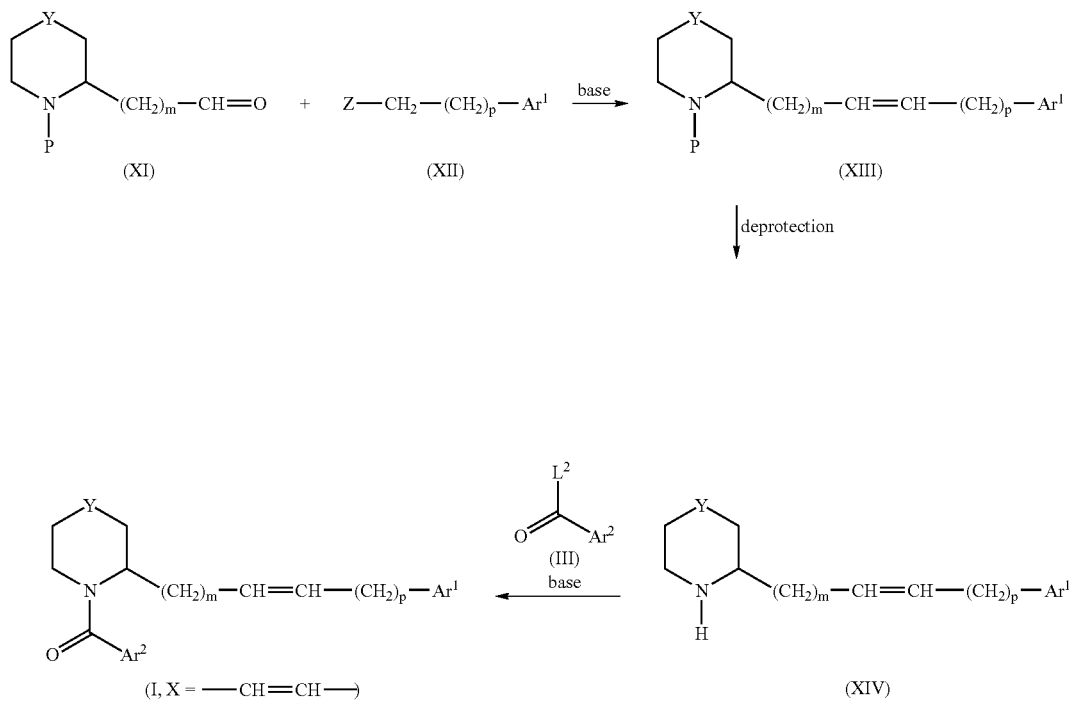

where Z represents a group [P$^+$(aryl)$_3$][Br$^-$] or a group P(=O)(Oalkyl)$_2$, and all other variables are as previously defined.

The reaction between (XI) and (XII) may be carried out in an inert solvent such as tetrahydroftran, in the presence of a base such as butyllithium. Deprotection and final coupling steps can be carried out in a manner similar to those described in Scheme 1.

Included within the scope is protecting group interchange and use of optional protecting groups within Ar$^1$, Ar$^2$, R$^1$, R$^2$, and Y for example when Y is NH, preferably a protecting group is used.

Compounds of formula (XI) and (XII) are known in the literature or can be prepared by known methods.

Compounds of formula (I) where X is C=O may be prepared by: reaction of a compound of formula (XI) with a compound W—(CH$_2$)$_p$—Ar$^1$, where W is the residue of an organometallic species, e.g. Li— or BrMg—, in an inert solvent such as tetrahydrofuran; followed by oxidation of the resulting secondary alcohol with an oxidant such as Dess Martin periodinane in an inert solvent such as dichloromethane; then deprotection and coupling of the resultant secondary amine with a compound of formula (III) in the manner previously described.

Alternatively compounds of formula (I) where X is C=O may be prepared by reaction of a compound of formula (XV)

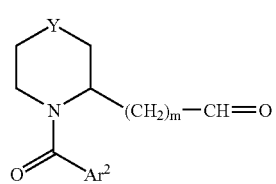

(XV)

wherein Y, m and Ar$^2$ are as defined for formula (I); with a compound W—(CH$_2$)$_p$—Ar$^1$ as defined above in an inert solvent such as tetrahydrofuran; followed by oxidation of the resulting secondary alcohol with an oxidant such as Dess Martin periodinane as described above. Compounds of formula (XV) are known in the literature or can be prepared by known methods.

The compounds of formula (I) may be prepared singly or as compound libraries comprising at least 2, e.g. 5 to 1000, preferably 10 to 100 compounds of formula (I). Compound libraries may be prepared by a combinatorial 'split and mix' approach or by multiple parallel synthesis using either solution phase or solid phase chemistry, by procedures known to those skilled in the art.

Thus according to a further aspect of the invention there is provided a compound library comprising at least 2 compounds of formula (I), or pharmaceutically acceptable salts thereof The present invention also includes isotopically-labeled compounds, which are identical to those recited in formulas (I) and following, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine, and chlorine, such as $^3$H, $^{11}$C, $^{14}$C, $^{18}$F, $^{123}$I and $^{125}$I.

Compounds of the present invention and pharmaceutically acceptable derivatives thereof of said compounds that contain the aforementioned isotopes and/or other isotopes of other atoms are within the scope of the present invention. Isotopically-labeled compounds of the present invention, for example those into which radioactive isotopes such as $^3$H, $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. $^{11}$C and $^8$F isotopes are particularly useful in PET (positron emission tomography), and $^{125}$I isotopes are particularly useful in SPECT (single photon emission computerized tomography), all useful in brain imaging. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of formula (I) and following of this invention can generally be prepared by carrying out the procedures disclosed in the Schemes and/or in the Examples below, by substituting a readily available isotopically labeled reagent for a non-isotopically labeled reagent.

Pharmaceutically acceptable salts may be prepared conventionally by reaction with the appropriate acid or acid derivative.

The compounds of formula (I) and their pharmaceutically acceptable salts are useful for the treatment of diseases or disorders where an antagonist of a human orexin receptor is required such as obesity and diabetes; prolactinoma; hypoprolactinemia; hypothalamic disorders of growth hormone deficiency; idiopathic growth hormone deficiency; Cushings syndrome/disease; hypothalamic-adrenal dysfunction; dwarfism; sleep disorders; sleep apnea; narcolepsy; insomnia; parasomnia; jet-lag syndrome; sleep disturbances associated with diseases such as neurological disorders, neuropathic pain and restless leg syndrome; heart and lung diseases; depression; anxiety; addictions; obsessive compulsive disorder; affective neurosis/disorder; depressive neurosis/disorder; anxiety neurosis; dysthymic disorder; behaviour disorder; mood disorder; sexual dysfunction; psychosexual dysfunction; sex disorder; sexual disorder; schizophrenia; manic depression; delerium; dementia; bulimia and hypopituitarism. The compounds of formula (I) or pharmaceutically acceptable derivatives thereof are also useful in the treatment of stroke, particular ischaemic or haemorrhagic stroke. Furthermore the compounds of formula (I) or pharmaceutically acceptable derivatives useful in the blocking an emetic response.

The compounds of formula (I) and their pharmaceutically acceptable salts are particularly useful for the treatment of obesity, including obesity associated with Type 2 diabetes, and sleep disorders. Additionally the compounds are useful in stroke and/or blocking the emetic response i.e. nausea and vomiting.

Other diseases or disorders which may be treated in accordance with the invention include disturbed biological and circadian rhythms; adrenohypophysis disease; hypophysis disease; hypophysis tumor/adenoma; adrenohypophysis hypofunction; functional or psychogenic amenorrhea; adrenohypophysis hyperfunction; migraine; hyperalgesia; pain; enhanced or exaggerated sensitivity to pain such as hyperalgesia, causalgia and allodynia; acute pain; burn pain; atypical facial pain; neuropathic pain; back pain; complex regional pain syndromes I and II; arthritic pain; sports injury pain; pain related to infection e.g. HIV, post-polio syndrome and post-herpetic neuralgia; phantom limb pain; labour pain; cancer pain; post-chemotherapy pain; post-stroke pain; post-operative pain; neuralgia; and tolerance to narcotics or withdrawal from narcotics.

The invention also provides a method of treating or preventing diseases or disorders where an antagonist of a human orexin receptor is required, which comprises administering to a subject in need thereof an effective amount of a compound of formula (I), or a pharmaceutically acceptable derivative thereof.

The invention also provides a compound of formula (I), or a pharmaceutically acceptable derivative thereof, for use in the treatment or prophylaxis of diseases or disorders where an antagonist of a human orexin receptor is required.

The invention also provides the use of a compound of formula (I), or a pharmaceutically acceptable derivative thereof, in the manufacture of a medicament for the treatment or prophylaxis of diseases or disorders where an antagonist of a human orexin receptor is required.

For use in therapy the compounds of the invention are usually administered as a pharmaceutical composition. The invention also provides a pharmaceutical composition comprising a compound of formula (I), or a pharmaceutically acceptable derivative thereof, and a pharmaceutically acceptable carrier.

The compounds of formula (I) and their pharmaceutically acceptable derivative may be administered by any convenient method, e.g. by oral, parenteral, buccal, sublingual, nasal, rectal or transdermal administration, and the pharmaceutical compositions adapted accordingly.

The compounds of formula (I) and their pharmaceutically acceptable derivative which are active when given orally can be formulated as liquids or solids, e.g. as syrups, suspensions, emulsions, tablets, capsules or lozenges.

A liquid formulation will generally consist of a suspension or solution of the active ingredient in a suitable liquid carrier(s) e.g. an aqueous solvent such as water, ethanol or glycerine, or a non-aqueous solvent, such as polyethylene glycol or an oil. The formulation may also contain a suspending agent, preservative, flavouring and/or colouring agent.

A composition in the form of a tablet can be prepared using any suitable pharmaceutical carrier(s) routinely used for preparing solid formulations, such as magnesium stearate, starch, lactose, sucrose and cellulose.

A composition in the form of a capsule can be prepared using routine encapsulation procedures, e.g. pellets containing the active ingredient can be prepared using standard carriers and then filled into a hard gelatin capsule; alternatively a dispersion or suspension can be prepared using any suitable pharmaceutical carrier(s), e.g. aqueous gums, celluloses, silicates or oils and the dispersion or suspension then filled into a soft gelatin capsule.

Typical parenteral compositions consist of a solution or suspension of the active ingredient in a sterile aqueous carrier or parenterally acceptable oil, e.g. polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active ingredient in a pharmaceutically acceptable aqueous or non-aqueous solvent and are usually presented in single or multidose quantities in sterile form in a sealed container which can take the form of a cartridge or refill for use with an atomising device. Alternatively the sealed container may be a disposable dispensing device such as a single dose nasal inhaler or an aerosol dispenser fitted with a metering valve. Where the dosage form comprises an aerosol dispenser, it will contain a propellant which can be a compressed gas e.g. air, or an organic propellant such as a fluorochlorohydrocarbon or hydrofluorocarbon. Aerosol dosage forms can also take the form of pump-atomisers.

Compositions suitable for buccal or sublingual administration include tablets, lozenges and pastilles where the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

Preferably the composition is in unit dose form such as a tablet, capsule or ampoule.

The dose of the compound of formula (I), or a pharmaceutically acceptable salt thereof, used in the treatment or prophylaxis of the abovementioned disorders or diseases will vary in the usual way with the particular disorder or disease being treated, the weight of the subject and other similar factors. However, as a general rule, suitable unit doses may be 0.05 to 1000 mg, more suitably 0.05 to 500 mg. Unit doses may be administered more than once a day for example two or three times a day, so that the total daily dosage is in the range of about 0.01 to 100 mg/kg; and such therapy may extend for a number of weeks or months. In the case of pharmaceutically acceptable salts the above figures are calculated as the parent compound of formula (I).

No toxicological effects are indicated/expected when a compound of formula (I) is administered in the above mentioned dosage range.

Human orexin-A has the amino acid sequence:

```
                                              (SEQ ID NO:1)
pyroGlu Pro Leu Pro Asp Cys Cys Arg Gln Lys Thr
1               5                   10

Cys Ser Cys Arg Leu Tyr Glu Leu Leu His Gly Ala
    15                          20

Gly Asn His Ala Ala Gly Ile Leu Thr Leu-NH₂
    25              30
```

Orexin-A can be employed in screening procedures for compounds which inhibit the ligand's activation of the orexin-1 receptor.

In general, such screening procedures involve providing appropriate cells which express the orexin-1 receptor on their surface. Such cells include cells from mammals, yeast, *Drosophila* or *E. coli*. In particular, a polynucleotide encoding the orexin-1 receptor is used to transfect cells to express the receptor. The expressed receptor is then contacted with a test compound and an orexin-1 receptor ligand to observe inhibition of a functional response. One such screening procedure involves the use of melanophores which are transfected to express the orexin-1 receptor, as described in WO 92/01810.

Another screening procedure involves introducing RNA encoding the orexin-1 receptor into *Xenopus* oocytes to transiently express the receptor. The receptor oocytes are then contacted with a receptor ligand and a test compound, followed by detection of inhibition of a signal in the case of screening for compounds which are thought to inhibit activation of the receptor by the ligand.

Another method involves screening for compounds which inhibit activation of the receptor by determining inhibition of binding of a labelled orexin-1 receptor ligand to cells which have the receptor on their surface. This method involves transfecting a eukaryotic cell with DNA encoding the orexin-1 receptor such that the cell expresses the receptor on its surface and contacting the cell or cell membrane preparation with a compound in the presence of a labelled form of an orexin-1 receptor ligand. The ligand may contain a radioactive label. The amount of labelled ligand bound to the receptors is measured, e.g. by measuring radioactivity.

Yet another screening technique involves the use of FLIPR equipment for high throughput screening of test compounds that inhibit mobilisation of intracellular calcium ions, or other ions, by affecting the interaction of an orexin-1 receptor ligand with the orexin-1 receptor.

All publications, including but not limited to patents and patent applications, cited in this specification are herein incorporated by reference as if each individual publication were specifically and individually indicated to be incorporated by reference herein as though fully set forth.

The following Examples illustrate the preparation of pharmacologically active compounds of the invention. The Descriptions D1-D20 illustrate the preparation of intermediates to compounds of the invention.

DESCRIPTION 1 tert-Butyl-N-(2-benzylaminoethyl)carbamate

Benzaldehyde (3.3 ml, 32.4 mmol) was added to a stirred solution of tert-butyl-N-(2-aminoethyl)carbamate (5.19 g, 32.4 mmol) in 1,2-dichloroethane (50 ml). After stirring for 1 h sodium triacetoxyborohydride (10.3 g, 48.6 mmol) was added in two portions and the reaction mixture stirred at room temperature for a further 3 h. Dichloromethane (300 ml) was added and the mixture washed with 1N sodium hydroxide. The organic layer was dried ($Na_2SO_4$) and evaporated in vacuo. The residue was chromatographed on silica gel eluting with 50-100% ethyl acetate in hexane then 1-5% methanol in ethyl acetate to afford the title compound (4.9 g, 60%). Mass spectrum ($AP^+$): Found 251 ($MH^+$). $C_{14}H_{22}N_2O_2$ requires 250.

DESCRIPTION 2

(E)-Ethyl-[4-(N-benzyl-N-(2-tert-butyloxycarbonylaminoethyl))-amino]but-2-enoate 75% Ethyl-4-bromocrotonate (5.04 g, 19.6 mmol) was added to a stirred mixture of tert-butyl-N-(2-benzylaminoethyl)carbamate (D1) (4.9 g, 19.6 mmol), potassium carbonate (3.06 g, 21.56 mmol) and potassium iodide (3.25 g, 19.6 mmol) in anhydrous dimethylformamide (100 ml) at room temperature under argon. After stirring for 18 h the reaction mixture was poured into water (750 ml) and extracted with diethyl ether (3×200 ml). Combined extracts were washed with water (250 ml), brine (250 ml), dried ($Na_2SO_4$) and evaporated in vacuo. Chromatography on silica gel eluting with 0-30% ethyl acetate in hexane gave the title compound as an orange oil (5.9 g 83%). $^1$H NMR ($CDCl_3$) δ: 1.30 (3H, t, J=7 Hz), 1.44 (9H, s), 2.56 (2H, t, J=6 Hz), 3.10-3.30 (4H, m), 3.60 (2H, s), 4.20 (2H, q, J=7 Hz), 4.80 (1H, broad m), 6.00 (1H, dd, J=1, 16 Hz), 6.85-7.10 (1H, dt, J=6, 16 Hz), 7.20-7.45 (5H, m).

DESCRIPTION 3

(RS)-Ethyl-(4-benzylpiperazin-2-yl)acetate

A solution of (E)-ethyl-[4-(N-benzyl-N-(2-tert-butyloxycarbonylaminoethyl))amino]but-2-enoate (D2) (5.9 g, 16.3 mmol) in dichloromethane (150 ml) and trifluoroacetic acid (30 ml) was stirred at room temperature for 2 h. The mixture was evaporated in vacuo and the residue partitioned between saturated potassium carbonate and dichloromethane (100 ml each). The aqueous layer was extracted with dichloromethane (4×50 ml) and the combined organics dried ($Na_2SO_4$) and evaporated in vacuo to afford the title compound as a brown oil (4.36 g, 100%). Mass spectrum ($AP^+$): Found 263 ($MH^+$). $C_{15}H_{22}N_2O_2$ requires 262.

DESCRIPTION 4

(RS)-4-Benzyl-2-(2-hydroxyethyl)piperazine

A 1M solution of lithium aluminium hydride in tetrahydrofuran (32.8 ml) was added dropwise to a stirred solution of (RS)-ethyl-(4-benzylpiperazin-2-yl)acetate (D3) (4.3 g, 16.41 mmol) in anhydrous tetrahydrofuran (100 ml) under argon, maintaining the temperature below 10° C. The resultant was stirred for a further 0.25 h, warmed to room temperature and stirred for 2.5 h. Water (8.2 ml), 2N sodium hydroxide (10.2 ml), and water (8.2 ml) were added dropwise sequentially with ice cooling. After 0.2 h sodium sulfate was added, the mixture stirred for 0.2 h then filtered through a short pad of celite. The filtrate was evaporated in vacuo to give the title compound as a pale orange oil (3.3 g, 91%). Mass spectrum ($AP^+$): Found 221 ($MH^+$). $C_{13}H_{20}N_2O$ requires 220.

DESCRIPTION 5

(RS)-4-Benzyl-1-(tert-butyloxycarbonyl)-2-(2-hydroxyethyl)piperazine

A solution of di-tert-butyl dicarbonate (3.3 g, 15.12 mmol) in dichloromethane (10 ml) was added to a stirred solution of (RS)-4-benzyl-2-(2-hydroxyethyl)piperazine (D4) (3.3 g, 15 mmol) at room temperature and the resultant stirred for a further 18 h. Evaporation in vacuo and chromatography of the residue on silica gel eluting with 10-50% ethyl acetate in hexane gave the title compound as a colourless oil (4.1 g, 85%). Mass spectrum ($AP^+$): Found 321 ($MH^+$). $C_{18}H_{28}N_2O_3$ requires 320.

DESCRIPTION 6

(RS)-1-(tert-Butyloxycarbonyl)-2-(2-hydroxyethyl)piperazine

A solution of (RS)-4-benzyl-1-(tert-butyloxycarbonyl)-2-(2-hydroxyethyl)piperazine (D5) (2.5 g, 7.81 mmol) in ethanol (150 ml) was hydrogenated at atmospheric pressure and room temperature in the presence of 10% palladium on charcoal (2.07 g, 54% paste with water) for 3.5 h. The mixture was filtered through Kieselguhr and the filtrate evaporated in vacuo to give the title compound as a colourless oil (1.65 g, 92%). Mass spectrum (AP$^+$): Found 231 (MH$^+$). $C_{11}H_{22}N_2O_3$ requires 230.

DESCRIPTION 7

(RS)-1-(tert-Butyloxycarbonyl)-2-(2-hydroxyethyl)-4-methoxycarbonylpiperazine

A solution of methyl chloroformate (0.52 ml, 6.73 mmol) in dichloromethane (5 ml) was added dropwise over 0.1 h to a stirred solution of (RS)-1-(tert-butyloxycarbonyl)-2-(2-hydroxyethyl)piperazine (D6) (1.4 g, 6.09 mmol) and triethylamine (1.7 ml, 12.2 mmol) in dichloromethane (45 ml) at 0° C. under argon. The resultant mixture was stirred at room temperature for 18 h, washed with saturated sodium hydrogen carbonate and the organic layer dried (Na$_2$SO$_4$) and evaporated in vacuo. The residue was chromatographed on silica gel eluting with 10-100% ethyl acetate in hexane to give the title compound as a colourless gum (1.36 g, 78%). $^1$H NMR (CDCl$_3$)δ: 1.48 (9H, s), 1.60-1.95 (2H, m), 2.80-3.00 (2H, m), 3.05-3.45 (2H, m), 3.50-3.70 (2H, m), 3.70 (3H, s), 3.75-4.45 (4H, m).

DESCRIPTION 8

(RS)-1-(tert-Butyloxycarbonyl)-4-methoxycarbonyl-2-(2-phenoxyethyl)piperazine

A solution of diethyl azodicarboxylate (0.74 ml, 4.7 mmol) in anhydrous dichloromethane (3 ml) was added to a stirred, ice-methanol cooled solution of (RS)-1-(tert-butoxycarbonyl)-2-(2-hydroxyethyl) -4-methoxycarbonylpiperazine (D7) (1.35 g, 4.69 mmol), phenol (0.441 g, 4.69 mmol) and triphenylphosphine (1.23 g, 4.69 mmol) in anhydrous dichloromethane (40 ml). The mixture was stirred at room temperature for 18 h then evaporated in vacuo. The residue was chromatographed on silica gel eluting with 10-20% ethyl acetate in hexane to give the title compound (1.43 g, 84%). $^1$H NMR (CDCl$_3$) δ: 1.38 (9H, m), 1.85-2.20 (2H, m), 2.75-3.20 (3H, m), 3.72 (3H, s), 3.80-4.20 (5H, m), 4.39 (1H, broad m), 6.75-7.00 (3H, m), 7.15-7.35 (2H, m).

DESCRIPTION 9

(RS)-4-Methoxycarbonyl-2-(2-phenoxyethyl)piperazine

A solution of (RS)-1-(tert-butyloxycarbonyl)-4-methoxycarbonyl-2-(2-phenoxyethyl)piperazine (D8) (1.4 g, 3.85 mmol) in dichloromethane (30 ml) and trifluoroacetic acid (5 ml) was stirred at 35° C. for 0.75 h. On cooling, the mixture was evaporated in vacuo and the residue partitioned between dichloromethane and IN sodium hydroxide (50 ml each). The organic layer was dried (Na$_2$SO$_4$) and evaporated in vacuo to afford the title compound as a colourless oil (1.01 g, 99%). Mass spectrum (AP$^+$): Found 265 (MH$^+$). $C_{14}H_{20}N_2O_3$ requires 264.

DESCRIPTION 10

(RS)-4-Methyl-2-(2-phenoxyethyl)piperazine

A 1M solution of lithium aluminium hydride in tetrahydrofuran (7.6 ml) was added dropwise to a stirred solution of (RS)-4-methoxycarbonyl-2-(2-phenoxyethyl)piperazine (D9) (1 g, 3.79 mmol) in anhydrous tetrahydrofuran (30 ml) at 0° C. under argon. The resultant mixture was stirred at 0° C. for 0.25 h and at room temperature for a further 1.5 h. Water (1.25 ml), 2N sodium hydroxide (1.55 ml) and water (1.25 ml) were added dropwise sequentially with ice cooling. After 0.2 h sodium sulphate was added, the mixture stirred for 0.2 h and then filtered through a short pad of celite. The filtrate was evaporated in vacuo to give the title compound as a colourless oil (0.73 g, 88%). Mass spectrum (AP$^+$): Found 221 (MH$^+$). $C_{13}H_{20}N_2O$ requires 220.

DESCRIPTION 11

(RS)-1-(tert-Butyloxycarbonyl)-2-(2-hydroxyethyl)-4-trifluoroacetyl-piperazine

Trifluoroacetic anhydride (1.08 ml, 7.65 mmol) was added dropwise to a stirred solution of (RS)-1-(tert-butyloxycarbonyl)-2-(2-hydroxyethyl)piperazine (D6) (1.6 g, 6.96 mmol) and triethylamine (1.2 ml, 8.35 mmol) in anhydrous dichloromethane (50 ml) at 0° C. under argon. The reaction mixture was allowed to warm to room temperature over 2 h, then stirred for 68 h. The mixture was washed with saturated sodium hydrogen carbonate, dried (Na$_2$SO$_4$) and evaporated in vacuo to give the title compound as a colourless solid (2.03 g, 99%). Mass spectrum (AP$^+$): Found 349 (MNa$^+$). $C_{13}H_{21}F_3N_2O_4$ requires 326.

DESCRIPTION 12

(RS)-1-(tert-Butyloxycarbonyl)-2-(2-(4-fluoro)phenoxyethyl)-4-trifluoroacetylpiperazine The title compound was prepared using the method of Description 8, from (RS)-1-(tert -butyloxycarbonyl)-2-(2-hydroxyethyl)-4-trifluoroacetylpiperazine (D11) (0.805 g, 2.47 mmol) and 4-fluorophenol (0.277 g, 2.47 mmol) as a colourless gum (0.41 g, 39%). Mass spectrum (AP$^+$): Found 443 (MNa$^+$). $C_{19}H_{24}F_4N_2O_4$ requires 420.

DESCRIPTION 13

(RS)-2-(2-(4-Fluoro)phenoxyethyl)-4-trifluoroacetylpiperazine

The title compound was prepared using the method of Description 9, from (RS)-1-(tert -butyloxycarbonyl)-2-(2-(4-fluoro)phenoxyethyl)-4-trifluoroacetylpiperazine (D12) (0.4 g, 0.95 mmol) as a pale yellow gum (0.16 g, 52%). Mass spectrum (AP$^+$): Found 321 (MH$^+$). $C_{14}H_{16}F_4N_2O_2$ requires 320.

DESCRIPTION 14

(RS)-2-(2-Hydroxyethyl)-4-(benzyloxycarbonyl)-1-tert-butyloxy -carbonyl)piperazine The title compound (2.0 g, 91%) was obtained from the compound of D6 (1.4 g, 6.09 mmol) and benzyl chloroformate (0.96 ml, 6.70 mmol) according to the method of D7. Mass spectrum (AP$^+$): Found 265 (MH-Boc$^+$). $C_{19}H_{28}N_2O_5$ requires 364.

DESCRIPTION 15

(RS)-4-(Benzyloxycarbonyl)-1-(tert-butyloxycarbonyl)-2-(2-phenoxyethyl)piperazine The title compound (2 g, 83%) was obtained from the compound of D14 (2 g, 5.49 mmol) and phenol (0.518 g, 5.49 mmol) according to the method of D8. Mass spectrum (AP$^+$): Found 341 (MH-Boc$^+$). $C_{25}H_{32}N_2O_5$ requires 440.

DESCRIPTION 16

(RS)-4-(Benzyloxycarbonyl)-2-(2-phenoxyethyl) piperazine

The title compound (0.66 g, 86%) was obtained from the compound of D15 (1 g, 2.3 mmol) according to the method of D9. Mass spectrum (AP$^+$): Found 341 (MH$^+$). $C_{20}H_{24}N_2O_3$ requires 340.

DESCRIPTION 17

(RS)-1-(tert-Butyloxycarbonyl)-2-(2-phenoxyethyl) piperazine

To the compound from D15 (0.95 g, 2.15 mmol) in ethanol (50 ml) was added 10% Pd/C catalyst (60% aqueous paste) (0.43 g) and the mixture hydrogenated at NTP for 3 h. The resultant was filtered through kieselguhr, washing well with ethanol and the filtrate evaporated to afford the title product (0.64 g, 97%) as an oily gum. Mass spectrum (AP$^+$): Found 307 (MH$^+$). $C_{17}H_{26}N_2O_3$ requires 306.

DESCRIPTION 18

(RS)-4-Acetyl-1-(tert-butyloxycarbonyl)-2-(2-phenoxyethyl)piperazine

The title compound (0.114 g, 99%) was obtained from the compound of D17 (0.100 g, 0.33 mmol) and acetyl chloride (0.035 ml, 0.49 mmol) according to the method of Example 2. Mass spectrum (AP$^+$): Found 349 (MH$^+$). $C_{19}H_{28}N_2O_4$ requires 348.

DESCRIPTION 19

(RS)-4-Acetyl-2-(2-phenoxyethyl)piperazine

The title compound (0.074 g, 99%) was obtained from the compound of D18 (0.1 g, 0.28 mmol) according to the method of D9. Mass spectrum (AP$^+$): Found 249 (MH$^+$) $C_{14}H_{20}N_2O_2$ requires 248.

DESCRIPTION 20

(RS)-4-(Benzyloxycarbonyl)-1-((2-phenyl)benzamido)-2-(2-phenoxyethyl)piperazine

The title compound (0.14 g, 83%) was obtained from the compound of D16 (0.11 g, 0.324 mmol) and 2-phenylbenzoyl chloride (0.077 g, 0.356 mmol) according to the method of Example 2. Mass spectrum (Electrospray LC/MS): Found 521 (MH$^+$). $C_{33}H_{32}N_2O_4$ requires 520.

EXAMPLE 1

(RS)-2-(2-(4-Fluoro)phenoxyethyl)-1-((4-(2-methyl-5-phenyl)thiazolyl)carbonyl)-4-trifluoroacetylpiperazine The title compound was prepared using the method of Example 2, from (RS)-2-(2-(4-fluoro)phenoxyethyl)-4-trifluoroacetyl piperazine (D13) (0.16 g, 0.5 mmol) as a pale orange gum (0.19 g, 73%). Mass spectrum (AP$^+$): Found 522 (MH$^+$). $C_{25}H_{23}F_4N_3O_3S$ requires 521.

EXAMPLE 2

(RS)-4-Methyl-1-((4-(2-methyl-5-phenyl)thiazolyl) carbonyl)-2-(2-phenoxyethyl) piperazine 2-Methyl-5-phenylthiazole-4-carbonyl chloride (0.029 g, 0.12 mmol) in dichloromethane (1 ml) was added to a solution of (RS)-4-methyl-2-(2-phenoxyethyl)piperazine (D10) (0.022 g, 0.1 mmol) and triethylamine (0.042 ml, 0.3 mmol) in dichloromethane (2 ml), and the mixture shaken for 1 h. The reaction mixture was washed with saturated sodium hydrogen carbonate (3 ml). The organic layer was added directly onto a 10 g pre-packed silica gel cartridge and eluted with 0-100% ethyl acetate in hexane to give the title compound as a colourless gum (0.021 g, 50%). Mass spectrum (Electrospray LC/MS): Found 422 (MH$^+$). $C_{24}H_{27}N_3O_2S$ requires 421.

EXAMPLE 3

(RS)-2-(2-(4-Fluoro)phenoxyethyl)-1-((4-(2-methyl-5-phenyl)thiazolyl) carbonyl)piperazine A mixture of (RS)-2-(2-(4-fluoro)phenoxyethyl)-1-((4-(2-methyl-5-phenyl)thiazolyl)carbonyl)-4-trifluoroacetylpiperazine (product of example 1) (0.18 g, 0.35 mmol) and potassium carbonate (0.3 g, 2.17 mmol) in methanol (6 ml) and water (2 ml) were heated at 80° C. for 2 h. On cooling the reaction mixture was evaporated in vacuo and the residue partitioned between dichloromethane (30 ml) and 1N sodium hydroxide (30 ml). The aqueous layer was extracted with dichloromethane (2×30 ml), the combined organics dried (Na$_2$SO$_4$) and evaporated in vacuo to afford the title compound as a brown gum (0.11 g, 74%). Mass spectrum (AP$^+$): Found 426 (MH$^+$). $C_{23}H_{24}FN_3O_2S$ requires 425.

EXAMPLE 4

(RS)-4-Methyl-2-(2-phenoxyethyl)-1-((2-phenyl) benzamido)-piperazine

The title compound (0.34 g, 85%) was obtained from the compound of D10 (0.022 g, 0.1 mmol) and 2-phenylbenzoyl chloride (0.022 g, 0.1 mmol) as described for Example 2. Mass spectrum (Electrospray LC/MS): Found 401 (MH$^+$). $C_{26}H_{28}N_2O_2$ requires 400.

EXAMPLE 5

(RS)-4-(Benzyloxycarbonyl)-1-((2-(3-methyl-[1,2,4]-oxadiazol-5-yl)-phenyl)carbonyl)-2-(2-phenoxyethyl)piperazine The title compound (0.138 g, 81%) was obtained from the compound of D16 (0.11 g, 0.32 mmol) and 2-(3-methyl-[1,2,4]-oxadiazol-5-yl)benzoyl chloride (0.079 g, 0.36 mmol) according to the method of Example 2. Mass spectrum (Electrospray LC/MS): Found 527 (MH$^+$). $C_{30}H_{30}N_4O_5$ requires 526.

EXAMPLE 6

(RS)-4-(Benzyloxycarbonyl)-1-((4-(2-methyl-5-phenyl)thiazolyl)carbonyl)-2-(2-phenoxyethyl)piperazine The title compound (0.16 g, 91%) was obtained from the compound of D16 (0.11 g, 0.32 mmol) and 2-methyl-5-phenylthiazole-4-carbonyl chloride (0.086 g, 0.36 mmol) according to the method of Example 2. Mass spectrum (Electrospray LC/MS): Found 542 (MH$^+$). $C_{31}H_{31}N_3O_4S$ requires 541.

EXAMPLE 7

(RS)-4-(Methoxycarbonyl)-1-((2-phenyl)benzamido)-2-(2-phenoxyethyl)piperazine

The title compound (0.027 g, 80%) was obtained from the compound of D9 (0.02 g, 0.076 mmol) and 2-phenylbenzoyl chloride (0.026 g, 0.12 mmol) according to the method of Example 2. Mass spectrum (AP$^+$): Found 445 (MH$^+$). $C_{27}H_{28}N_2O_4$ requires 444.

EXAMPLE 8

(RS)-4-(Methoxycarbonyl)-1-((4-(2-methyl-5-phenyl)thiazolyl)carbonyl)-2-(2-phenoxyethyl)piperazine The title compound (0.031 g, 88%) was obtained from the compound of D9 (0.02 g, 0.076 mmol) and 2-methyl-5-phenylthiazole-4-carbonyl chloride (0.029 g, 0.12 mmol) according to the method of Example 2. Mass spectrum (AP$^+$): Found 466 (MH$^+$). $C_{25}H_{27}N_3O_4S$ requires 465.

EXAMPLE 9

(RS)-4-(Methoxycarbonyl)-1-((1-naphthyl)carbonyl)-2-(2-phenoxyethyl)piperazine

The title compound (0.019 g, 59%) was obtained from the compound of D9 (0.02 g, 0.076 mmol) and 1-naphthylcarbonyl chloride (0.023 g, 0.12 mmol) according to the method of Example 2. Mass spectrum (AP$^+$): Found 419 (MH$^+$). $C_{25}H_{26}N_2O_4$ requires 418.

EXAMPLE 10

(RS)-4-Acetyl-1-((4-(2-methyl-5-phenyl)thiazolyl)carbonyl)-2-(2-phenoxyethyl)piperazine The title compound (0.059 g, 88%) was obtained from the compound of D19 (0.037 g, 0.149 mmol) and 2-methyl-5-phenylthiazole-4-carbonyl chloride (0.043 g, 0.179 mmol) according to the method of Example 2. Mass spectrum (AP$^+$): Found 450 (MH$^+$). $C_{25}H_{27}N_3O_3S$ requires 449.

EXAMPLE 11

(RS)-1-((2-Phenyl)benzamido)-2-(2-phenoxyethyl)piperazine acetate

The compound of D20 (0.1 g, 0.19 mmol) in ethanol (10 ml) containing g. acetic acid (1 ml) was hydrogenated at NTP over 10% Pd/C (60% aq. paste) (0.03 g) for 5 h. The resultant was filtered through kieselguhr, washed with ethanol and the filtrate evaporated to afford the title product (0.07 g, 80%). Mass spectrum (Electrospray LC/MS): Found 387 (MH$^+$). $C_{25}H_{26}N_2O_2$ requires 386.

It is understood that the present invention covers all combinations of particular and preferred groups described herein above.

Determination of Orexin-1 Receptor Antagonist Activity

The orexin-1 receptor antagonist activity of the compounds of formula (I) was determined in accordance with the following experimental method.

Experimental Method

HEK293 cells expressing the human orexin-1 receptor were grown in cell medium (MEM medium with Earl's salts) containing 2 mM L-Glutamine, 0.4 mg/mL G418 Sulphate from GIBCO BRL and 10% heat inactivated fetal calf serum from Gibco BRL. The cells were seeded at 20,000 cells/100 μl/well into 96-well black clear bottom sterile plates from Costar which had been pre-coated with 10 μg/well of poly-L-lysine from SIGMA. The seeded plates were incubated overnight at 37° C. in 5% $CO_2$.

Agonists were prepared as 1 mM stocks in water:DMSO (1:1). $EC_{50}$ values (the concentration required to produce 50% maximal response) were estimated using 11× half log unit dilutions (Biomek 2000, Beckman) in Tyrode's buffer containing probenecid (10 mM HEPES with 145 mM NaCl, 10 mM glucose, 2.5 mM KCl, 1.5 mM $CaCl_2$, 1.2 mM $MgCl_2$ and 2.5 mM probenecid; pH7.4). Antagonists were prepared as 10 mM stocks in DMSO (100%). Antagonist $IC_{50}$ values (the concentration of compound needed to inhibit 50% of the agonist response) were determined against 3.0 nM human orexin-A using 11× half log unit dilutions in Tyrode's buffer containing 10% DMSO and probenecid.

On the day of assay 50 μl of cell medium containing probenecid (Sigma) and Fluo3AM (Texas Fluorescence Laboratories) was added (Quadra, Tomtec) to each well to give final concentrations of 2.5 mM and 4 μM, respectively. The 96-well plates were incubated for 90 min at 37° C. in 5% $CO_2$. The loading solution containing dye was then aspirated and cells were washed with 4×150 μl Tyrode's buffer containing probenecid and 0.1% gelatin (Denley Cell Wash). The volume of buffer left in each well was 125 μl. Antagonist or buffer (25 μl) was added (Quadra) the cell plates gently shaken and incubated at 37° C. in 5% $CO_2$ for 30 min. Cell plates were then transferred to the Fluorescent Imaging Plate Reader (FLIPR, Molecular Devices) instrument and maintained at 37° C. in humidified air. Prior to drug addition a single image of the cell plate was taken (signal test), to evaluate dye loading consistency. The run protocol used 60 images taken at 1 second intervals followed by a further 24 images at 5 second intervals. Agonists were added (by the FLIPR) after 20 sec (during continuous reading). From each well, peak fluorescence was determined over the whole assay period and the mean of readings 1-19 inclusive was subtracted from this figure. The peak increase in fluorescence was plotted against compound concentration and iteratively curve fitted using a four parameter logistic fit (as described by Bowen and Jerman, TiPS, 1995, 16, 413-417) to generate a concentrationeffect value. Antagonist Kb values were calculated using the equation:

$$K_b = IC_{50}/(1+([3/EC_{50}])$$

where $EC_{50}$ was the potency of human orexin-A determined in the assay (in nM terms) and $IC_{50}$ is expressed in molar terms.

Compounds of Examples tested according to this method had pKb values in the range 7.0-8.5 at the human cloned orexin-1 receptor.

The orexin-2 receptor antagonist activity of the compounds of formula (I) is determined in accordance with the following experimental method.

Experimental Method

CHO-DG44 cells expressing the human orexin-2 receptor were grown in cell medium (MEM medium with Earl's salts) containing 2 mM L-Glutamine, 0.4 mg/mL G418 Sulphate from GIBCO BRL and 10% heat inactivated fetal calf serum from Gibco BRL. The cells were seeded at 20,000 cells/100 μl/well into 96-well black clear bottom sterile plates from Costar which had been pre-coated with 10 μg/well of poly-L-lysine from SIGMA. The seeded plates were incubated overnight at 37 C in 5% $CO_2$.

Agonists were prepared as 1 mM stocks in water:DMSO (1:1). EC50 values (the concentration required to produce 50% maximal response) were estimated using 11× half log unit dilutions (Biomek 2000, Beckman) in Tyrode's buffer containing probenecid (10 mM HEPES with 145 mM NaCl, 10 mM glucose, 2.5 mM KCl, 1.5 mM $CaCl_2$, 1.2 mM $MgCl_2$ and 2.5 mM probenecid; pH7.4). Antagonists were prepared as 10 mM stocks in DMSO (100%). Antagonist IC50 values (the concentration of compound needed to inhibit 50% of the agonist response) were determined against 10.0 nM human orexin-A using 11× half log unit dilutions in Tyrode's buffer containing 10% DMSO and probenecid.

On the day of assay 50 μl of cell medium containing probenecid (Sigma) and Fluo3AM (Texas Fluorescence Laboratories) was added (Quadra, Tomtec) to each well to give final concentrations of 2.5 mM and 4 μM, respectively. The 96-well plates were incubated for 60 min at 37 C in 5% $CO_2$. The loading solution containing dye was then aspirated and cells were washed with 4×150 μl Tyrode's buffer containing probenecid and 0.1% gelatin (Denley Cell Wash). The volume of buffer left in each well was 125 μl. Antagonist or buffer (25 μl) was added (Quadra) the cell plates gently shaken and incubated at 37 C in 5% $CO_2$ for 30 min. Cell plates were then transferred to the Fluorescent Imaging Plate Reader (FLIPR, Molecular Devices) instrument. Prior to drug addition a single image of the cell plate was taken (signal test), to evaluate dye loading consistency. The run protocol used 60 images taken at 1 second intervals followed by a further 24 images at 5 second intervals. Agonists were added (by the FLIPR) after 20 sec (during continuous reading). From each well, peak fluorescence was determined over the whole assay period and the mean of readings 1-19 inclusive was subtracted from this figure. The peak increase in fluorescence was plotted against compound concentration and iteratively curve fitted using a four parameter logistic fit (as described by Bowen and Jennan, TiPS, 1995, 16, 413-417) to generate a concentration effect value. Antagonist Kb values were calculated using the equation:

$$Kb = IC50/(1+([3/EC50])$$

where EC50 was the potency of human orexin-A determined in the assay (in nM terms) and $IC_{50}$ is expressed in molar terms.

Compounds of Examples tested according to this method had pkb values of less than 7 at the human orexin-2 receptor.

Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation the following claims.

The invention claimed is:
1. A compound of formula (I):

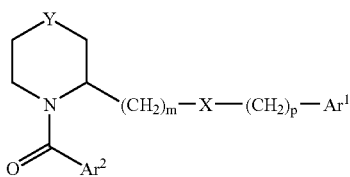

(I)

wherein:
Y represents $NR^2$;
m represents 1, 2, or 3;
p represents 0 or 1;
X is O, S, C=O, $SO_2$, or —CH=CH—;
$Ar^1$ is an optionally substituted phenyl, naphthyl, quinoxalinyl, quinazolinyl, pyridopyrazinyl, benzoxazolyl, benzothiophenyl, benzimidazolyl, naphthyridinyl, pyridinyl, pyrimidinyl, thiazolyl, or benzofuranyl group;
$Ar^2$ represents a phenyl group or a 5- or 6-membered heterocyclyl group, wherein the phenyl or heterocyclyl group is substituted by $R^1$ and further optional substituents, and wherein said heterocyclyl group is selected from furanyl, thienyl, pyrrolyl, oxazolyl, thiazolyl, imidazolyl, oxadiazolyl, thiadiazolyl, pyridinyl, triazolyl, triazinyl, pyridazinyl, pyrimidinyl, isothiazolyl, isoxazolyl, pyrazinyl, and pyrazolyl; or
$Ar^2$ represents an optionally substituted group selected from benzofuranyl, benzimidazolyl, quinolinyl, quinoxalinyl, and naphthyl;
$R^1$ represents a trifluoromethoxy, methoxy, halo, or an optionally substituted phenyl, pyridinyl, pyrazolyl, oxadiazolyl, or pyrimidinyl group;
$R^2$ represents hydrogen or $(C_{1-4})$alkyl;
wherein the optional substituents for the optionally substituted groups of $Ar^1$, $Ar^2$ and $R^1$ are selected from the group consisting of halogen, hydroxy, oxo, cyano, nitro, $(C_{1-4})$ alkyl, $(C_{1-4})$alkoxy, halo$(C_{1-4})$alkyl, halo$(C_{1-4})$alkoxy, aryl$(C_{1-4})$alkoxy, $(C_{1-4})$alkylthio, hydroxy$(C_{1-4})$ alkyl, $(C_{1-4})$alkoxy$(C_{1-4})$alkyl, $(C_{3-6})$cycloalkyl$(C_{1-4})$alkoxy, $(C_{1-4})$alkanoyl, $(C_{1-4})$alkoxycarbonyl, $(C_{1-4})$alkylsulfonyl, $(C_{1-4})$alkylsulfonyloxy, $(C_{1-4})$alkylsulfonyl$(C_{1-4})$alkyl, arylsulfonyl, arylsulfonyloxy, arylsulfonyl$(C_{1-4})$alkyl, $(C_{1-4})$alkylsulfonamido, $(C_{1-4})$alkylamido, $(C_{1-4})$alkylsulfonamido$(C_{1-4})$alkyl, $(C_{1-4})$alkylamido$(C_{1-4})$alkyl, arylsulfonamido, arylcarboxamido, arylsulfonamido$(C_{1-4})$alkyl, arylcarboxamido$(C_{1-4})$alkyl, aroyl, aroyl$(C_{1-4})$alkyl, aryl$(C_{1-4})$alkanoyl, $(C_{1-4})$acyl, aryl, aryl$(C_{1-4})$alkyl, $(C_{1-4})$alkylamino$(C_{1-4})$alkyl, and $R^3R^4N$—, $R^3OCO(CH_2)_r$, $R^3CON(R^4)(CH_2)_r$, $R^3R^4NCO(CH_2)_r$, $R^3R^4NSO_2(CH_2)_r$, and $R^3SO_2NR^4(CH_2)_r$ wherein each of $R^3$ and $R^4$ independently represents a hydrogen atom or a $(C_{1-4})$alkyl group and r represents zero or an integer from 1 to 4;
or a pharmaceutically acceptable salt thereof.

2. A compound according to claim 1, wherein $R_2$ represents hydrogen, methyl, or ethyl.
3. A compound according to in claim 1, wherein $Ar^2$ represents optionally substituted phenyl, pyridinyl, thiazolyl, pyrazolyl, pyridazinyl, 1,2,3-triazolyl or naphthyl.
4. A compound according to claim 1, wherein $Ar^1$ represents an optionally substituted phenyl.
5. A compound according to claim 4, wherein optional substituents for said optionally substituted phenyl are selected from halogen, cyano, $C_{1-4}$alkanoyl, and $C_{1-4}$alkylsulfonyl.
6. A compound according to claim 3, wherein said optionally substituted phenyl, pyridinyl, thiazolyl, pyrazolyl, pyridazinyl, 1,2,3-triazolyl or naphthyl is substituted by one group selected from halogen, cyano, $(C_{1-4})$alkanoyl, and $(C_{1-6})$ alkyl.
7. A compound according to claim 4, wherein said optionally substituted phenyl is substituted by halogen.
8. A compound according to claim 1 wherein m is 2 and p is 0.
9. A compound according to claim 1 wherein X is O.
10. A pharmaceutical composition comprising the compound according to claim 1, or a pharmaceutically acceptable salt thereof, and a pharmaceutically acceptable carrier.
11. A method of treating a disease or disorder where an antagonist of a human orexin receptor is required, which comprises administering to a subject in need thereof an effective amount of the compound according to claim 1, or a pharmaceutically acceptable salt thereof, wherein said disease or disorder is selected from obesity and obesity associated with Type II diabetes.
12. A method of treating a disease or disorder where an antagonist of a human orexin receptor is required, which comprises administering to a subject in need thereof an effective amount of the compound according to claim 1, or a pharmaceutically acceptable salt thereof, wherein said disease or disorder is selected from sleep apnea, insomnia, parasomnia and jet-lag syndrome.
13. A method of treating a disease or disorder where an antagonist of a human orexin receptor is required, which comprises administering to a subject in need thereof an effective amount of the compound according to claim 1, or a pharmaceutically acceptable salt thereof, wherein said disease or disorder is insomnia.
14. A compound according to claim 1, wherein $R^1$ represents an optionally substituted phenyl.

* * * * *

SEQUENCE LISTING

<160> NUMBER OF SEQ ID NOS: 1

<210> SEQ ID NO 1
<211> LENGTH: 35
<212> TYPE: PRT
<213> ORGANISM: Human orexin A

<400> SEQUENCE: 1

Glu Pro Leu Pro Asp Cys Cys Arg Gln Lys Thr Cys Ser Cys Arg Leu
1               5                   10                  15

Tyr Glu Leu Leu His Gly Ala Gly Asn His Ala Ala Gly Ile Leu Thr
            20                  25                  30

Leu Asn His
        35